(12) United States Patent
Hsieh et al.

(10) Patent No.: US 9,610,316 B2
(45) Date of Patent: Apr. 4, 2017

(54) MEDICAL COMPOSITION FOR INHIBITING THE GROWTH OF CANCER STEM CELLS

(71) Applicant: National Taiwan Normal University, Taipei (TW)

(72) Inventors: Hsiu-Mei Hsieh, Taipei (TW); Chen-Yu Lee, Taipei (TW)

(73) Assignee: NATIONAL TAIWAN NORMAL UNIVERSITY (TW)

( * ) Notice: Subject to any disclaimer, the term of this patent is extended or adjusted under 35 U.S.C. 154(b) by 142 days.

(21) Appl. No.: 14/138,253

(22) Filed: Dec. 23, 2013

(65) Prior Publication Data

US 2014/0106013 A1    Apr. 17, 2014

Related U.S. Application Data

(63) Continuation of application No. 12/926,302, filed on Nov. 9, 2010, now abandoned.

(30) Foreign Application Priority Data

Jan. 20, 2010 (TW) ............................... 99101774 A (51) Int. Cl.
| | | |
|---|---|---|
| A61K 36/65 | (2006.01) | |
| A61K 36/756 | (2006.01) | |
| A61K 36/232 | (2006.01) | |
| A61K 36/284 | (2006.01) | |
| A61K 36/484 | (2006.01) | |
| A61K 36/539 | (2006.01) | |
| A61K 36/71 | (2006.01) | |
| A61K 36/718 | (2006.01) | |
| A61K 36/744 | (2006.01) | |
| A61K 36/804 | (2006.01) | |

(52) U.S. Cl.
CPC .......... *A61K 36/756* (2013.01); *A61K 36/232* (2013.01); *A61K 36/284* (2013.01); *A61K 36/484* (2013.01); *A61K 36/539* (2013.01); *A61K 36/65* (2013.01); *A61K 36/71* (2013.01); *A61K 36/718* (2013.01); *A61K 36/744* (2013.01); *A61K 36/804* (2013.01)

(58) Field of Classification Search
None
See application file for complete search history.

(56) References Cited

U.S. PATENT DOCUMENTS

| | | | | |
|---|---|---|---|---|
| 2003/0035851 A1* | 2/2003 | Chen | .................. | A61K 31/352 424/728 |
| 2004/0109904 A1* | 6/2004 | Li | .................. | 424/725 |
| 2004/0142001 A1 | 7/2004 | Kuok et al. | | |
| 2004/0219508 A1 | 11/2004 | Schwartz | | |
| 2006/0052438 A1* | 3/2006 | Ho et al. | ........ | 514/453 |
| 2006/0079575 A1* | 4/2006 | Lin et al. | ........ | 514/464 |

FOREIGN PATENT DOCUMENTS

| | | | |
|---|---|---|---|
| CN | 1095933 A | | 12/1994 |
| CN | 101264164 A | | 9/2008 |
| CN | 101357202 A | * | 2/2009 |
| CN | 101485823 A | * | 7/2009 |
| TW | 200806307 A | | 2/2008 |

OTHER PUBLICATIONS 2014 http://flowers.la.coocan.jp/Asteraceae/Atractylodes%20japonica.htm.*
2015 http://www.shen-nong.com/eng/herbal/gancao.html.*
http://www.nybg.org/plants/plants/gardenia.html.*
Cancer.gov 2016 http://www.cancer.gov/about-cancer/what-is-cancer/metastatic-fact-sheet.*
Shao Jin-Ming, Determination of ferulic acid and other two constituents by HPLC in different decoctions of Qingwei San, China hospital pharmacy journal, 2008, p. 868-870, vol. 28 No. 11, China Academic Journal Electronic Publishing House.
Pao-Hsin Liao, Shiow-Ling Chen, Hung-Che Shih and Ming-Yung Chou, Induction of apoptosis in human oral cancer cell lines, OC2 and TSCCa, by Chingwaysan, The American Journal of Chinese Medicine, 2005, p. 21-27, vol. 33, No. 1, World Scientific Publishing Company, Taiwan.
Qiu-Bai Li, Yong You, Zhi-Chao Chen, Jing Shao, Jian Lu and Ping Zou, Proliferation inhibiting and apoptosis inducing effect of huanglian-jie-du-tang (HLJDT) on human myeloma RPMI8226 cells, Journal of Leukemia & Lymphoma, 2006, p. 412-415, vol. 15, No. 6, China.
GanSu University of Traditional Chinese Medicine, Study of Pharmaceutical Mechanism of Huang Lian Jie Du Tang, Chinese Journal of Clinical Medicine, 2008, vol. 7, No. 3, China.
Effects of Modified Huang Lian Jie Du Tang on Cells of Human Multiple Myeloma Cell Line RPMI8226, Traditional Chinese Medicine integrated with Western Medicine, 2008, China.
Tetsuo Yajima, Hiromi Ochiai, Takeshi Uchiy Ama, Nobuo Takano, Takahiko Shibahara and Toshifumi Azuma, Resistance to cytotoxic chemotherapy-induced apoptosis in side population cells of human oral squamous cell carcinoma cell line Ho-1-N-1, International Journal of Oncology, 2009, p. 273-280, Japan.
New meanings for recipes in rhymes;10. Chingwaysan, Mar. 1985, Taiwan.
PH Liao,SL Chen,HC Shih and MY Chou,Induction of apoptosis in human oral cancer cell lines, OC2 and TSCCa by Chingwaysan, American Journal of Chinese Medicine, vol. 33, Iss.1, p. 21-27, 2005, Taiwan.

(Continued)

*Primary Examiner* — Terry A McKelvey
*Assistant Examiner* — Catheryne Chen
(74) *Attorney, Agent, or Firm* — Bacon & Thomas, PLLC (57) ABSTRACT

A medical composition for inhibiting the growth of cancer stem cells is disclosed. The medical composition is prepared by mixing herbal medicines with water or alcohol, followed by heating and extraction to obtain a filtrate. One of the medical compositions according to the present invention includes: *Coptis chinensis, Scutellaria baicalensis, Phellodendron amourense, Gardenia jasminoides, Radix Glycyrrhizae,* and *Atractylodes japonica*.

14 Claims, 6 Drawing Sheets

(56) References Cited

OTHER PUBLICATIONS

EJ, Choi and GH, Kim, Atractylodes japonica Rhizome Inhibits Cell Proliferation and Induces Apoptosis in vitro, Food Science and Biotechnology, vol. 18, Iss. 4, p. 1019-1021, 2009.

Studies of Huanglian jiedu decoction by modern medical science methods, The Journal of Taiwan Pharmacy, vol. 25, Iss. 4, Jan. 2010.
Studies related to Huanglian jiedu decoction, Oct. 2010.
Atradctylodes japonica. [Retrieved from the internet on: Oct. 22, 2011]. Retrieved from: <URL:http://flowers.la.coocan.jp/Asteraceae/Atractylodes%20japonica.htm>.

* cited by examiner

MEDICAL COMPOSITION FOR INHIBITING THE GROWTH OF CANCER STEM CELLS

CROSS REFERENCE TO RELATED APPLICATIONS

This application is a continuation of U.S. patent application Ser. No. 12/926,302, filed Nov. 9, 2010, which claims benefit to Taiwanese Application No. 99101774, filed Jan. 20, 2010, the entire contents which are incorporated herein by reference.

BACKGROUND OF THE INVENTION

1. Field of the Invention

The present invention relates to a medical composition for inhibiting the growth of cancer stem cells, which is capable of inhibiting the growth of cancer stem cells in addition to common cancer cells.

2. Description of Related Art

Cancer has always been one of ten leading causes of death but has increased in its perniciousness to become the first cause of death for 27 years. The main factor causing cancer is that cells become abnormal and keep dividing to form more cells, resulting in cancer.

Western medicine therapy for treatment of cancer, such as surgery, radiation therapy, chemotherapy, hormone therapy and biopharmaceutical therapy, is notorious for the distressing side-effects on patients. In view of those difficulties, more and more people opt for the less-radical Chinese medicine therapy. However, for both Chinese and Western medicine therapy, the commercial anticancer drugs can inhibit only growth of cancer cells, i.e., not cancer stem cells.

Cancer stem cells present in tumors are not large in amount, but they are highly resistant to drugs and can generate more cancer cells through cell division resulting in tumors. The aforementioned fact is a thorny problem in treating cancer. The Western chemotherapeutic drugs nowadays can kill only common cancer cells, and cannot efficiently inhibit growth of cancer stem cells. That is, a great amount of standard cancer treatment known in biomedicine has no influence on cancer stem cells. Thereby, to efficiently inhibit growth of cancer stem cells is inevitably advantageous to cancer treatment.

In general, Chinese herbal medicine is considered more moderate and more acceptable than Western chemical forms on the market. Although some clinical treatment results suggest that parts of medical compositions for treating cancer cells are indeed capable of controlling cancer, the efficiency of these medical compositions in inhibiting cancer cells as well as cancer stem cells has not been confirmed.

Accordingly, to develop a medical composition that has the confirmed efficiency in inhibiting cancer cells, particularly the growth of precursor cells (i.e. cancer stem cells), is helpful to cancer treatment.

SUMMARY OF THE INVENTION

The object of the present invention is to provide a medical composition capable of inhibiting growth of cancer stem cells. Also, the medical composition according to the present invention can inhibit growth of common cancer cells.

To achieve the object, the present invention provides a medical composition for inhibiting the growth of cancer stem cells including: an extract provided by mixing *Coptis chinensis, Scutellaria baicalensis, Phellodendron amourense, Gardenia jasminoides, Radix Glycyrrhizae*, and *Atractylodes japonica* with a water-containing solution or an alcohol-containing solution, followed by heating and extraction.

In the medical composition, *Coptis chinensis* ranges from 3 to 5 weight parts, *Scutellaria baicalensis* ranges from 3 to 5 weight parts, *Phellodendron amourense* ranges from 3 to 5 weight parts, *Gardenia jasminoides* ranges from 3 to 5 weight parts, *Radix Glycyrrhizae* ranges from 3 to 5 weight parts, and *Atractylodes japonica* ranges from 3 to 5 weight parts.

In addition, the present invention further provides a medical composition for inhibiting the growth of cancer stem cells including: an extract provided by mixing *Coptis chinensis, Rhizoma cimicifugae, Angelica sinensis*, Rhizome of *rehmannia*, and Cortex Moutan Radicis with a water-containing solution or an alcohol-containing solution, followed by heating and extraction.

In the medical composition, *Coptis chinensis* ranges from 3 to 5 weight parts, *Rhizoma cimicifugae* ranges from 3 to 5 weight parts, *Angelica sinensis* ranges from 3 to 5 weight parts, Rhizome of *rehamnnia* ranges from 3 to 5 weight parts, and Cortex Moutan Radicis ranges from 3 to 5 weight parts.

The above-mentioned medical compositions are prepared by heating and extraction with a water-containing or alcohol-containing solution. In the case of using an alcohol-containing solution, preferably, the alcohol-containing solution contains alcohol in 20-40%. In addition, during extraction, the solution containing the Chinese herb materials may be heated up to 70° C. or more. Preferably, the solution containing the Chinese herb materials is heated up to 70° C. or more and subjected to extraction for at least 60 minutes. Accordingly, the medical composition according to the present invention can be obtained.

DETAILED DESCRIPTION OF THE PREFERRED EMBODIMENT

In the following examples according to the present invention, A549 cancer cell survival is characterized after treatment with the medical compositions according to the present invention. Then, the arresting stage of cell cycle by use of these medical compositions according to the present invention is identified by flow cytometric analysis. In addition, the cell apoptosis resulted from the medical compositions according to the present invention is studied through cell staining. Moreover, the efficiency of the medical compositions according to the present invention killing cancer stem cells is evaluated by double fluorescence staining and flow cyometric analyses.

Example 1

*Coptis chinensis* (10 g), *Scutellaria baicalensis* (10 g), *Phellodendron amourense* (10 g), *Gardenia jasminoides* (10 g), *Radix Glycyrrhizae* (10 g), and *Atractylodes japonica* (10 g) are cut into slices and mixed with water to perform heating and extraction to obtain an extract. Herein, the heating is performed for 90 minutes at 70° C. Accordingly, the resulting extract is the medical composition according to the present example.

Test Example 1

Cell Survival Rate Test

Figure 1:
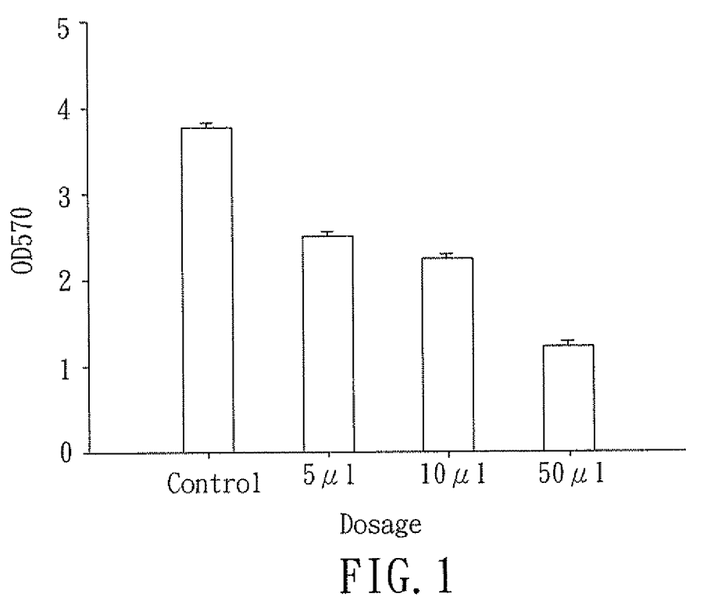
FIG. 1 is a statistical chart for showing the cell survival rates of lung cancer cells after treatment with various dosages of the medical composition according to Example 1 of the present invention.

A549 lung cancer cell survival rate is characterized through MTT assay after treatment with 5 μl, 10 μl and 50 μl of the medical composition according to Example 1 for 72 hours, respectively. The results are shown in FIG. 1. Herein, the horizontal axis represents a control group and various dosages of medical compositions, and the vertical axis represents the absorption of cells at 570 nm, which depends on the cell survival rate.

FIG. 1 shows that the increased dosage of the medical composition causes the reduction of A549 cancer cell survival rate after treatment for 72 hours. In addition, it can be inferred from FIG. 1 that the dose for 50% inhibition (ID50) of the medical composition according to Example 1 on A549 cells is 20 μl.

Test Example 2

Cell Survival Rate Test

Figure 2:
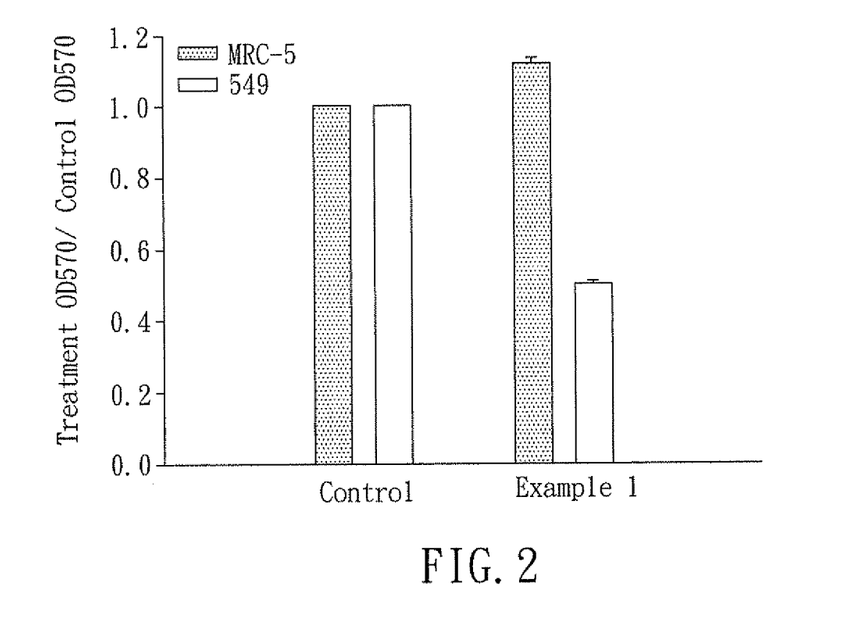
FIG. 2 is a statistical chart for showing the cell survival rates of lung cancer cells and normal cells after treatment with the medical composition according to Example 1 of the present invention.
Figure 3:
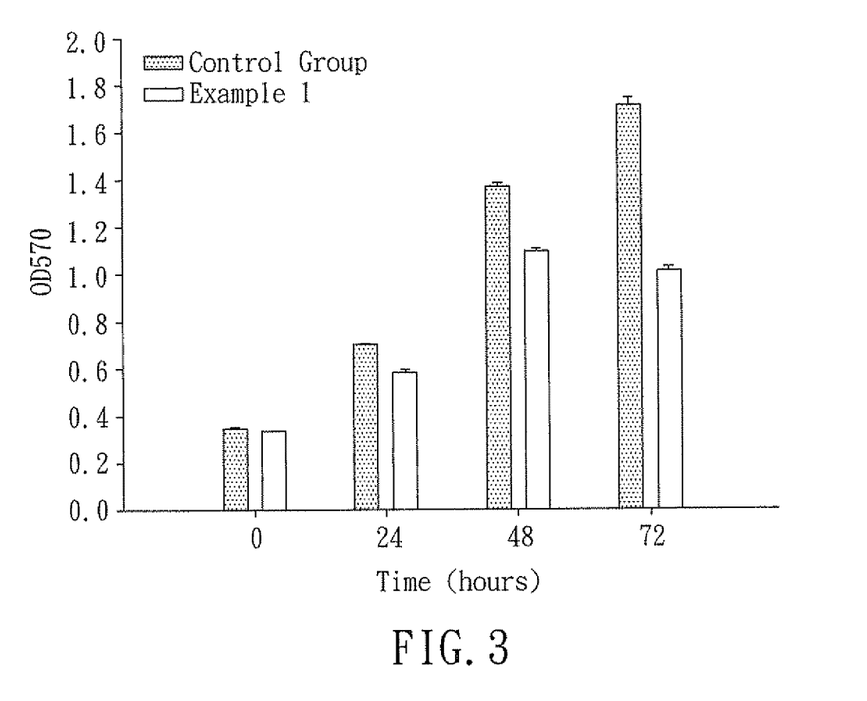
FIG. 3 is a chart for showing the correlation between treatment time and the lung cancer cell survival rate after treatment with the dose for 50% inhibition (ID50) of the medical composition according to Example 1.

After A549 lung cancer cells and MRC-5 normal cells are treated with 20 μl of the medical composition according to Example 1 for 72 hours, respectively, the cell survival rates thereof are characterized by MTT assay. The results are shown in FIGS. 2 and 3. FIG. 2 is a statistical chart showing the survival rates of the lung cancer cells and the normal cells after treatment with the medical composition according to Example 1. FIG. 3 is a chart showing the correlation between treatment time and the lung cancer cell survival rate after treatment with the dose for 50% inhibition (ID50) of the medical composition according to Example 1.

FIG. 2 suggests that the A549 lung cancer cell survival rate is significantly reduced with no decrease of the MRC-5 cell survival rate after treatment with the dose for 50% inhibition (ID50) of the medical composition according to Example 1 for 72 hours. Thereby, the medical composition according to Example 1 can significantly inhibit the growth of cancer cells but not the growth of normal cells.

FIG. 3 shows that the survival rate of A549 lung cancer cells is significantly reduced after treatment with ID50 of the medical composition according to Example 1 for 24, 48 and 72 hours in comparison with the A549 lung cancer cells with no treatment with the medical composition according to Example 1. Meanwhile, the variation of the cell survival rate increases with the increase of time.

Test Example 3

Arresting Stage of Cell Cycle Test

Figure 4:
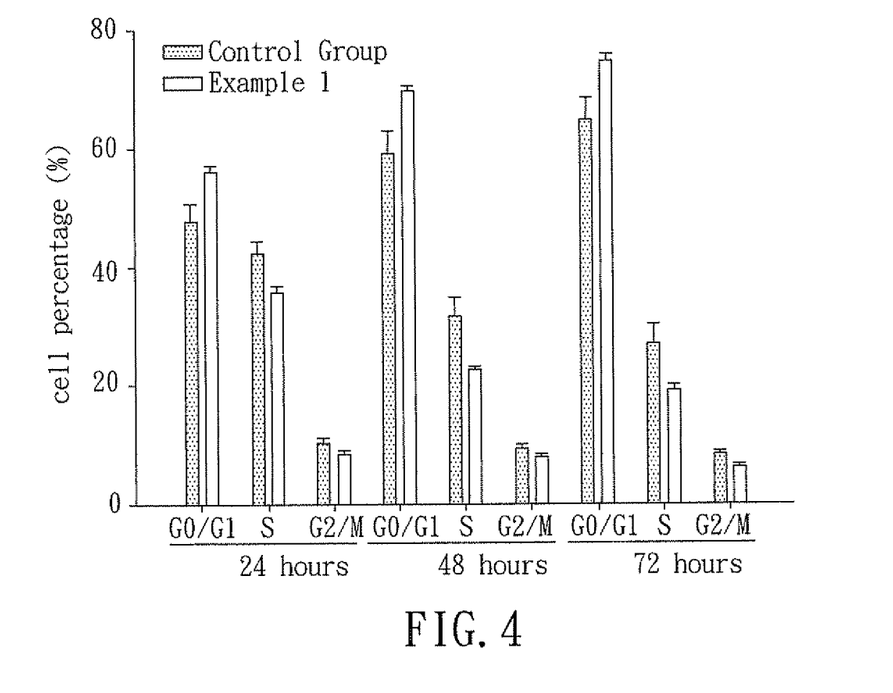
FIG. 4 is a statistical chart for showing the percentage of lung cancer cells in each cycle stage after treatment with the medical composition according to Example 1 of the present invention.

A549 lung cancer cells are PI stained after treatment with 20 μl (ID50) of the medical composition according to Example 1 for 72 hours. Subsequently, the DNA content of the lung cancer cells is detected by flow cytometric analysis to determine cell cycle distribution of lung cancer cells. The quantitative statistical results are shown in FIG. 4. Herein, the G0/G1, S and G2/M on the horizontal axis represent various cell cycle stages, respectively, and the vertical axis represents the percentage of cells in each cycle stage.

FIG. 4 suggests that the cell percentage in the G0/G1 stage significantly increases in the lung cancer cells treated with the medical composition according to Example 1 for 24, 48 and 72 hours, in comparison with the lung cancer cells without treatment with the medical composition according to Example 1. Thereby, it is confirmed that the medical composition according to Example 1 causes A549 lung cancer cells to be arrested in the G0/G1 stage.

Test Example 4

Arresting Stage of Cell Cycle Test

A549 lung cancer cells are double stained with PI and Ki67 antibody and observed by flow cytometric analysis to determine cell percentage of lung cancer cells in G0 stage after treatment with 20 μl (ID50) of the medical composition according to Example 1 for 72 hours.

Figure 5:
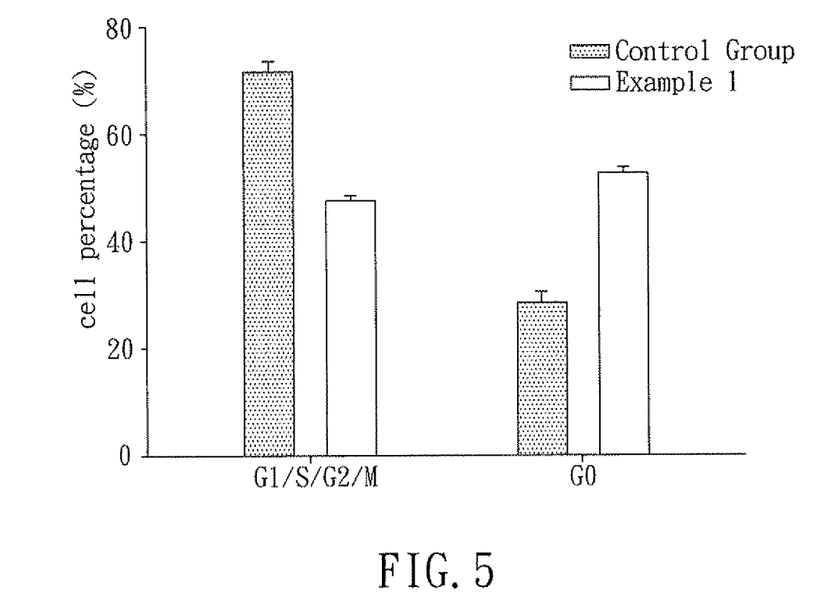
FIG. 5 is a statistical chart for showing the percentage of lung cancer cells in the G0 stage after treatment with the medical composition according to Example 1 of the present invention.

FIG. 5 suggests that the cell percentage in the G0 stage significantly increased in the lung cancer cells treated with the medical composition according to Example 1, in comparison with the lung cancer cells without treatment with the medical composition according to Example 1. Thereby, it is confirmed that more A549 cells can leave the cell cycle and stay in the quiescent G0 stage after treatment with the medical composition according to Example 1.

Test Example 5

Cancer Stem Cell Ratio Test

A549 lung cancer cells are stained with Hoechst33342 in the presence or absence of reserpine after treatment with 20 μl (ID50) of the medical composition according to Example 1 for 72 hours. The ratio of side population (SP) cells (i.e. cancer stem cells) is evaluated by flow cytometric analysis. Reserpine is used to inhibit ABCG2-mediated Hoechst33342 dye efflux. Accordingly, SP cancer stem cells in which ABCG2 is highly expressed can be identified by comparing the presence/absence of reserpine.

Figure 6:
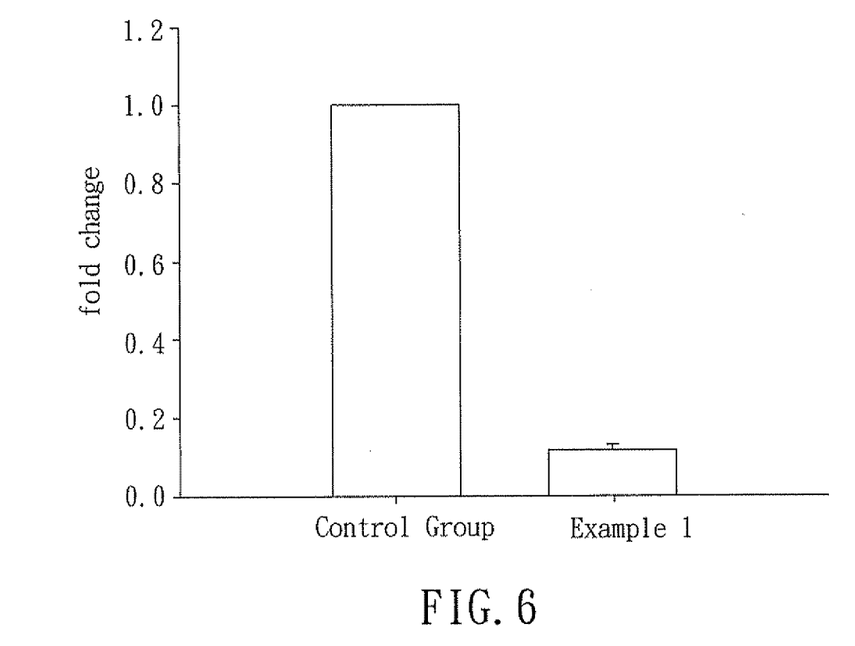
FIG. 6 is a statistical chart for showing the fold change of cancer stem cells after treatment with the medical composition according to Example 1 of the present invention.

The quantitative statistical results are shown in FIG. 6. Herein, the horizontal axis represents a fold change, i.e. the ratio of the measured value in the presence of reserpine to that in its absence. FIG. 6 suggests that the fold change can be reduced to about 0.1 after treatment with the medical composition according to Example 1. That is, the SP cancer stem cell mass is lower and the ratio of the cancer stem cells is significantly reduced. Thereby, it is confirmed that the medical composition according to Example 1 can inhibit the growth of cancer stem cells.

EXAMPLE 2

*Coptis chinensis* (10 g), *Rhizoma cumicifugae* (10 g), *Angelica sinensis* (10 g), Rhizome of *rehmannia* (10 g) and Cortex Moutan Radicis (10 g) are cut into slices and mixed with water to perform heating and extraction to obtain an extract. Herein, the heating is performed for 90 minutes at 70° C. Accordingly, the resulting extract is the medical composition according to the present example.

Test Example 6

Cell Survival Rate Test

The test method according to the present test example is the same as that of Test Example 1, except that the medical composition according to Example 1 is replaced by that according to Example 2. The results are shown in FIG. 7.

Figure 7:
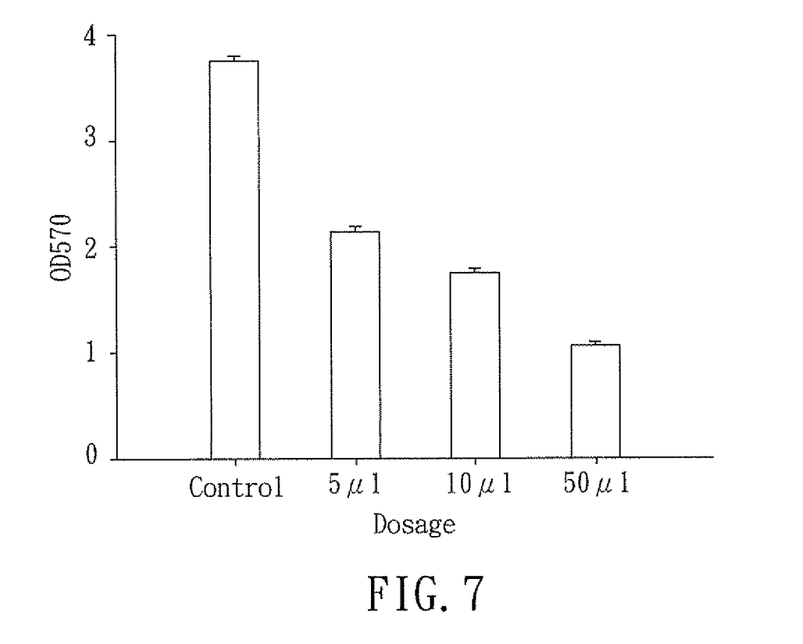
FIG. 7 is a statistical chart for showing the cell survival rates of lung cancer cells after treatment with various dosages of the medical composition according to Example 2 of the present invention.

FIG. 7 shows that the increased dosage of the medical composition causes the reduction of A549 cancer cell survival rate after treatment for 72 hours. In addition, it can be inferred from FIG. 7 that the dose for 50% inhibition (ID50) of the medical composition according to Example 2 on A549 cells is 11 μl.

Test Example 7

Cell Survival Rate Test

The test method according to the present test example is the same as that of Test Example 2, except that 20 μl of the medical composition according to Example 1 is replaced by 11 μl of the medical composition according to Example 2. The results are shown in FIGS. 8 and 9.

Figure 8:
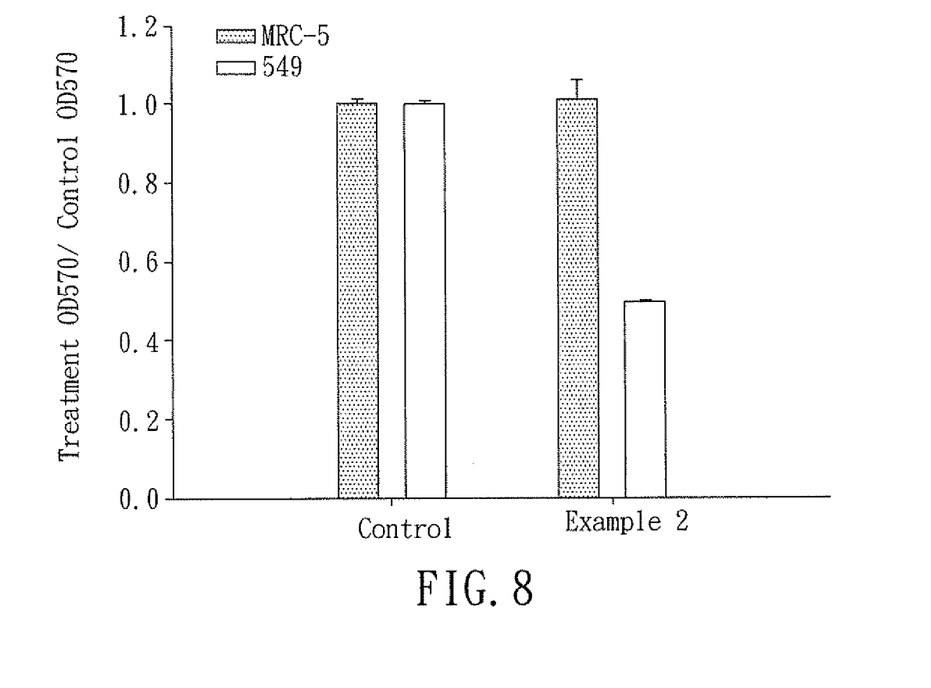
FIG. 8 is a statistical chart for showing the cell survival rates of lung cancer cells and normal cells after treatment with the medical composition according to Example 2 of the present invention.

FIG. 8 suggests that the A549 lung cancer cell survival rate is significantly reduced with no decrease of the MRC-5 cell survival rate after treatment with the dose for 50% inhibition (ID50) of the medical composition according to Example 2 for 72 hours.

Figure 9:
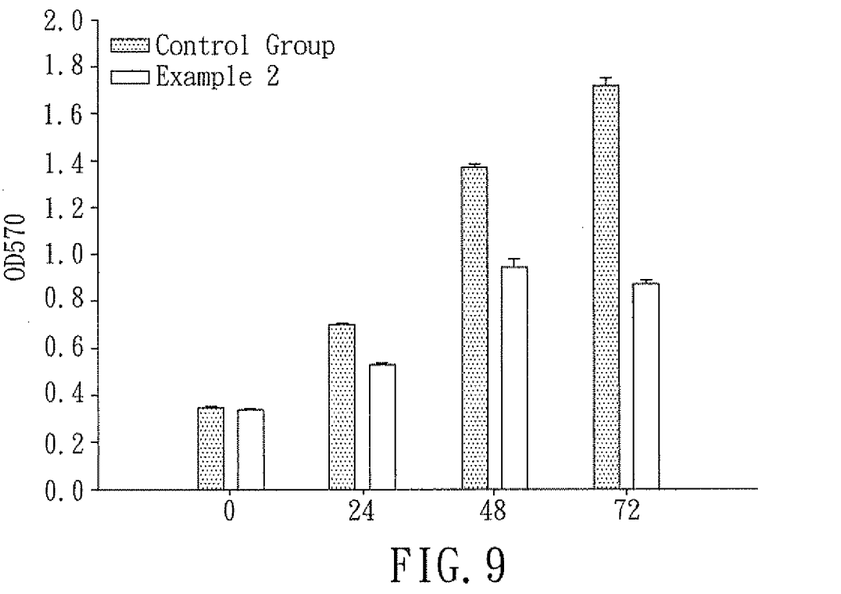
FIG. 9 is a chart for showing the correlation between treatment time and the lung cancer cell survival rate after treatment with the dose for 50% inhibition (ID50) of the medical composition according to Example 2.

FIG. 9 shows that the survival rate of A549 lung cancer cells is significantly reduced after treatment with ID50 of the medical composition according to Example 2 for 24, 48 and 72 hours in comparison with the A549 lung cancer cells with no treatment with the medical composition according to Example 2. Meanwhile, the variation of the, cell survival rate increases with the increase of time.

Test Example 8

Arresting Stage of Cell Cycle Test

Figure 10:
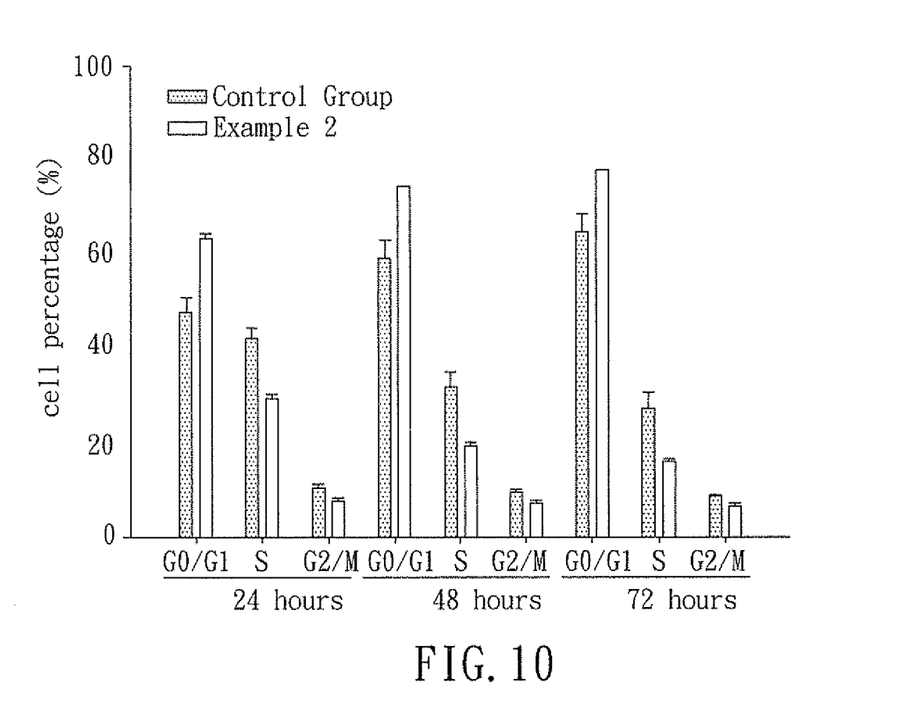
FIG. 10 is a statistical chart for showing the percentage of lung cancer cells in each cycle stage after treatment with the medical composition according to Example 2 of the present invention.

The test method according to the present test example is the same as that of Test Example 3, except that 20 μl of the medical composition according to Example 1 is replaced by 11 μl of the medical composition according to Example 2, The quantitative statistical results are shown in FIG. 10.

FIG. 10 suggests that the cell percentage in the G0/G1 stage significantly increases regarding the lung cancer cells treated with the medical composition according to Example 2 far 24, 48 and 72 hours, in comparison with the lung cancer cells of the control group without treatment with the medical composition according to Example 2. Thereby, it is confirmed that the medical composition according to Example 2 causes A549 lung cancer cells to be arrested in the G0/G1 stage.

Test Example 9

Arresting Stage of Cell Cycle Test

The test method according to the present test example is the same as that of Test Example 4, except that 20 μl of the medical composition according to Example 1 is replaced by 11 μl of the medical composition according to Example 2. The quantitative statistical results are shown in FIG. 11.

Figure 11:
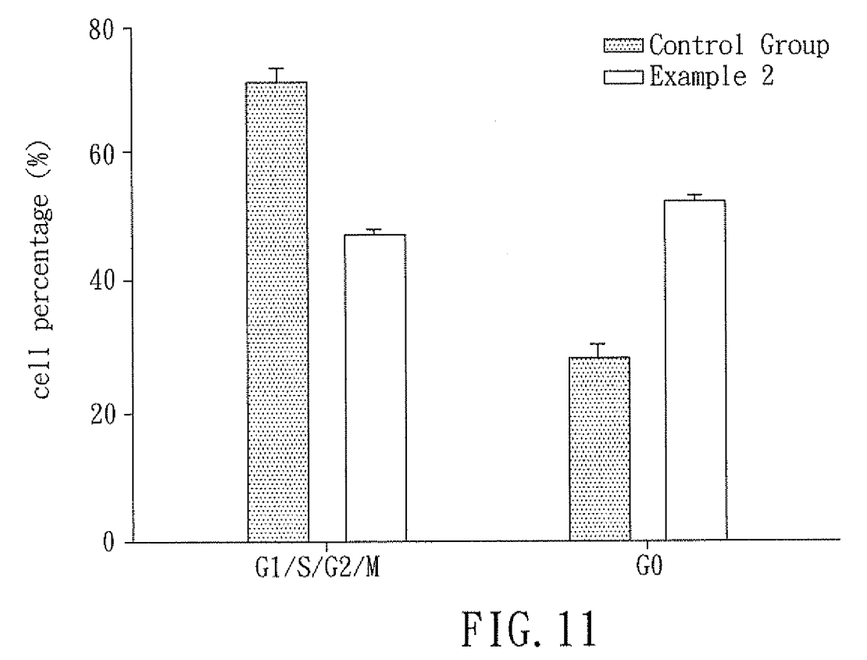
FIG. 11 is a statistical chart for showing the percentage of lung cancer cells in the G0 stage after treatment with the medical composition according to Example 2 of the present invention.

FIG. 11 suggests that the cell percentage in the G0 stage significantly increases regarding the lung cancer cells treated with the medical composition according to Example 2, in comparison with the lung cancer cells without treatment with the medical composition according to Example 2. Thereby, it is confirmed that more A549 cells can leave the cell cycle and stay in the quiescent G0 stage after treatment with the medical composition according to Example 2.

Test Example 10

Cancer Stem Cell Ratio Test

The test method according to the present test example is the same as that of Test Example 5, except that 20 μl of the medical composition according to Example 1 is replaced by 11 μl of the medical composition according to Example 2. The quantitative statistical results are shown in FIG. 12.

Figure 12:
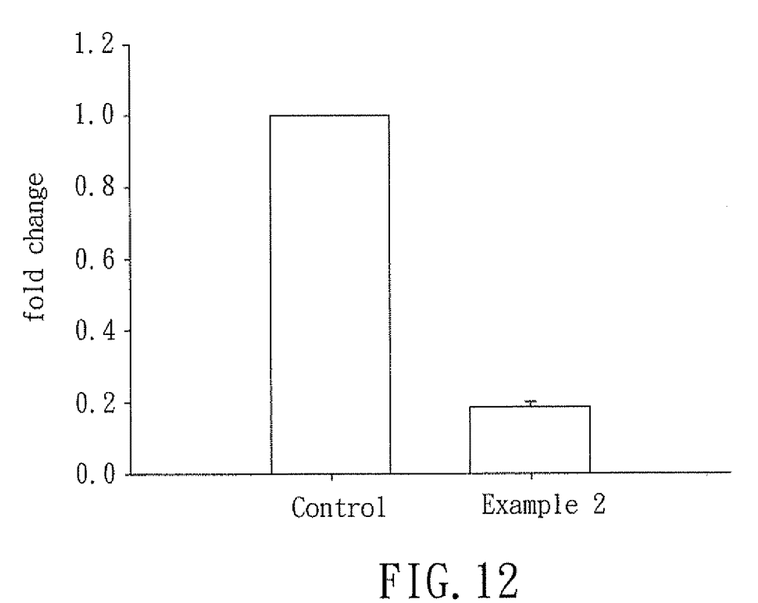
FIG. 12 is a statistical chart for showing the fold change of cancer stem cells after treatment with the medical composition according to Example 2 of the present invention.

FIG. 12 suggests that the fold change can be reduced to about 0.2 after treatment with the medical composition according to Example 2. That is, the SP cancer stem cell mass is lower and the ratio of the cancer stem cells is significantly reduced. Thereby, it is confirmed that the medical composition according to Example 2 can inhibit the growth of cancer stem cells.

From the results of Test Examples 1 to 10, it can be confirmed that the medical composition according to the present invention can inhibit the growth of cancer cells as well as cancer stem cells.

Although the present invention has been explained in relation to its preferred embodiment, it is to be understood that many other possible modifications and variations can be made without departing from the scope of the invention as hereinafter claimed.

What is claimed is:

1. A method for treating lung cancer, comprising:
administering a medical composition to a subject in need thereof to reduce cancer stem cells in the subject, wherein said medical composition consists essentially of: an extract provided by mixing *Coptis chinensis, Scutellaria baicalensis, Phellodendron amourense, Gardenia jasminoides, Radix Glycyrrhizae*, and *Atractylodes japonica* with a water-containing solution or an alcohol-containing solution, followed by heating and extraction.

2. The method of claim 1, wherein the *Coptis chinensis* ranges from 3 to 5 weight parts, the *Scutellaria baicalensis* ranges from 3 to 5 weight parts, the *Phellodendron amourense* ranges from 3 to 5 weight parts, the *Gardenia jasminoides* ranges from 3 to 5 weight parts, the *Radix Glycyrrhizae* ranges from 3 to 5 weight parts, and the *Atractylodes japonica* ranges from 3 to 5 weight parts.

3. The method of claim 1, wherein the alcohol-containing solution contains alcohol in 20-40%.

4. The method of claim 1, wherein the extract is prepared by heating to 70° C. or more and extraction with the water-containing or alcohol-containing solution.

5. The method of claim 1, wherein the extract is prepared by heating to 70° C. or more and extraction with the water-containing or alcohol-containing solution for at least 60 minutes.

6. A method for treating lung cancer, comprising:
administering a medical composition to a subject in need thereof to reduce cancer stem cells in the subject, wherein said medical composition consists essentially of: an extract provided by mixing *Coptis chinensis, Rhizoma cimicifugae, Angelica sinensis*, Rhizome of *rehmannia*, and Cortex Moutan Radicis with a water-containing solution or an alcohol-containing solution, followed by heating and extraction.

7. The method of claim 6, wherein the *Coptis chinensis* ranges from 3 to 5 weight parts, the *Rhizoma cimicifugae* ranges from 3 to 5 weight parts, the *Angelica sinensis* ranges from 3 to 5 weight parts, the Rhizome of *rehmannia* ranges from 3 to 5 weight parts, and the Cortex Moutan Radicis ranges from 3 to 5 weight parts.

8. The method of claim 6, wherein the alcohol-containing solution contains alcohol in 20-40%.

9. The method of claim 6, wherein the extract is prepared by heating to 70° C. or more and extraction with the water-containing or alcohol-containing solution.

10. The method of claim 6, wherein the extract is prepared by heating to 70° C. or more and extraction with the water-containing or alcohol-containing solution for at least 60 minutes.

11. The method of claim 1, wherein growth of cancer stem cells in the subject in need thereof is inhibited.

12. The method of claim 6, wherein growth of cancer stem cells in the subject in need thereof is inhibited.

13. The method of claim 1, wherein said medical composition consists of: an extract provided by mixing *Coptis chinensis, Scutellaria baicalensis, Phellodendron amourense, Gardenia jasminoides, Radix Glycyrrhizae*, and *Atractylodes* japonica with a water-containing solution or an alcohol-containing solution, followed by heating and extraction.

14. The method of claim 6, wherein said medical composition consists of: an extract provided by mixing *Coptis chinensis, Rhizoma cimicifugae, Angelica sinensis*, Rhizome of *rehmannia*, and Cortex Moutan Radicis with a water-containing solution or an alcohol-containing solution, followed by heating and extraction.

* * * * *

UNITED STATES PATENT AND TRADEMARK OFFICE
CERTIFICATE OF CORRECTION

PATENT NO. : 9,610,316 B2
APPLICATION NO. : 14/138253
DATED : April 4, 2017
INVENTOR(S) : Hsiu-Mei Hsieh et al.

Page 1 of 1

It is certified that error appears in the above-identified patent and that said Letters Patent is hereby corrected as shown below:

(71) Applicant should read: National Taiwan Normal University, Taipei (TW) and Chen-Yu LEE Taipei (TW)

(73) Assignee should read: NATIONAL TAIWAN NORMAL UNIVERSITY (TW) and CHEN-YU LEE (TW)

(30) Foreign Application Priority Data should read: Jan. 22, 2010 (TW) ................... 99101774 A Signed and Sealed this
Twelfth Day of December, 2017

Joseph Matal
*Performing the Functions and Duties of the
Under Secretary of Commerce for Intellectual Property and
Director of the United States Patent and Trademark Office*